(12) United States Patent
Miller

(10) Patent No.: US 12,311,065 B1
(45) Date of Patent: May 27, 2025

(54) SMART STERILIZATION DEVICE FOR CERTIFIED DISINFECTION OF PORTABLE ELECTRONIC DEVICES AND PERSONAL ITEMS

(71) Applicant: MobileDemand LC, Hiawatha, IA (US)

(72) Inventor: Matthew D. Miller, Cedar Rapids, IA (US)

(73) Assignee: MobileDemand LC, Hiawatha, IA (US)

( * ) Notice: Subject to any disclaimer, the term of this patent is extended or adjusted under 35 U.S.C. 154(b) by 971 days.

(21) Appl. No.: 17/349,555

(22) Filed: Jun. 16, 2021

Related U.S. Application Data

(60) Provisional application No. 63/039,516, filed on Jun. 16, 2020.

(51) Int. Cl.
*A61L 2/10* (2006.01)

(52) U.S. Cl.
CPC ............. *A61L 2/10* (2013.01); *A61L 2202/11* (2013.01); *A61L 2202/122* (2013.01); *A61L 2202/14* (2013.01)

(58) Field of Classification Search
CPC ..... A61L 2/10; A61L 2202/11; A61L 2202/14
See application file for complete search history.

(56) References Cited

U.S. PATENT DOCUMENTS

| | | | |
|---|---|---|---|
| 8,689,461 B1 * | 4/2014 | Cookson | F26B 3/205 219/229 |
| 2013/0063922 A1 * | 3/2013 | La Porte | A61L 2/10 250/455.11 |
| 2016/0088868 A1 * | 3/2016 | Dobrinsky | A23L 3/28 250/492.1 |

* cited by examiner

*Primary Examiner* — Sean E Conley
(74) *Attorney, Agent, or Firm* — Suiter Swantz IP

(57) ABSTRACT

A smart device and method for certified sterilization of personal computing/communications devices (e.g., smartphones, tablets, phablets) and other like personal effects provides an interior sterilization chamber fully or partially enclosed by a housing. The smart device includes an object tray or receptacle situated within the chamber for sterilization of any objects secured therein. Within the sterilization chamber, illuminators direct ultraviolet-C (UV-C) or other like disinfecting radiation at the external surfaces of the object according to a predetermined sterilization cycle or program. The selected sterilization cycle is executed by controlling the activation and/or articulation of the illuminators and/or the object tray or receptacle (either or both of which may be articulated to maximize the irradiated surface area of the object). When a sterilization cycle is complete, the control processors generate a unique token memorializing the successful completion of the cycle upon the sterilized object (e.g., a uniquely identified mobile device).

17 Claims, 12 Drawing Sheets

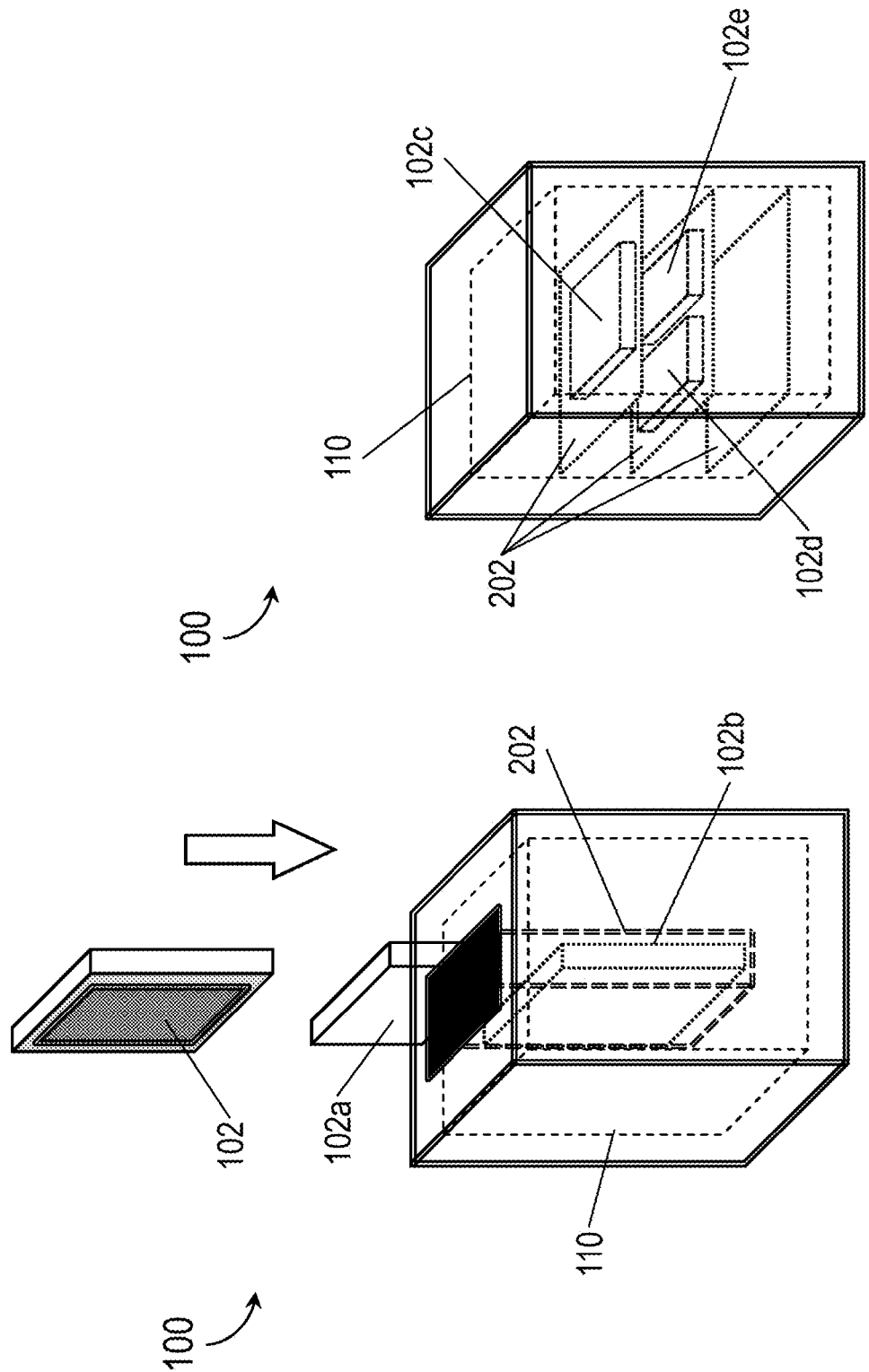

SMART STERILIZATION DEVICE FOR CERTIFIED DISINFECTION OF PORTABLE ELECTRONIC DEVICES AND PERSONAL ITEMS

CROSS-REFERENCE TO RELATED APPLICATIONS

The present application is related to and claims the benefit of the earliest available effective filing dates from the following listed applications (the "Related Applications") (e.g., claims earliest available priority dates for other than provisional patent applications (e.g., under 35 USC § 120 as a continuation in part) or claims benefits under 35 USC § 119 (e) for provisional patent applications, for any and all parent, grandparent, great-grandparent, etc. applications of the Related Applications).

RELATED APPLICATIONS

U.S. Provisional Patent Application Ser. No. 63/039,516 entitled APPARATUS FOR CERTIFIED STERILIZATION OF PORTABLE ELECTRONIC DEVICES AND PERSONAL ITEMS and filed Jun. 16, 2020;

Said U.S. Patent Application 63/039,516 is herein incorporated by reference in its entirety.

BACKGROUND

Personal mobile communication devices—smartphones, tablets, phablets, and other like mobile devices—have become an almost constant presence for personal, commercial, and official use. For example, a user may carry such a device in hand or on their person through a variety of locations and into the vicinity of dozens if not hundreds of people in the course of a normal day. In the process, the mobile device can become a breeding ground for any number of bacteria, viruses, or other pathogens which may survive for an extended amount of time on its surfaces, and which the user may rarely think to clean off on a regular basis. While this presents a clear hazard to the user, as the mobile device may be in close contact with their own hands or face continually throughout the day, the COVID-19 pandemic has served as a reminder that mobile devices may also serve as a means of spreading pathogens to new populations.

This may be especially true in applications, such as "contactless" shopping, package delivery, law enforcement, or other operations where a mobile terminal or other like device may be shared by (and may come into close contact with) multiple individuals in lieu of human contact between them. Compounding the problem, the spread of potentially dangerous and highly contagious pathogens through a population may be difficult to trace but, at the same time, present a fertile environment for liability claims based on any device (or owner/operator thereof) with the potential to be a vector.

SUMMARY

In a first aspect, a smart device for certified sterilization of personal computing/communications devices (e.g., smartphones, tablets, phablets) and other like personal effects is disclosed. In embodiments, the smart device includes a housing fully or partially enclosing an interior sterilization chamber. The smart device includes an object tray or receptacle for securing the object to be sterilized. When the tray or receptacle is outside the sterilization chamber, the object to be sterilized may be inserted or removed; the receptacle is manually or automatically retracted into the chamber for sterilization of any objects secured therein. Within the sterilization chamber, illuminators sterilize the object by directing ultraviolet-C (UV-C) or other like disinfecting radiation at the external surfaces of the object according to a predetermined sterilization cycle. Control processors initiate and execute the selected sterilization cycle by controlling the activation and/or articulation of the illuminators and/or the object tray (either or both of which may be articulated to maximize the irradiated surface area of the object). When a sterilization cycle is complete, the control processors generate a unique token memorializing the completion of the sterilization cycle upon the sterilized object.

In some embodiments, the smart device uniquely identifies the target object, and the unique token specifically corresponds to the identified object.

In some embodiments, the smart device includes cameras, scanners, and other sensors externally mounted, the sensors capable of detecting and identifying the target object (e.g., via image capture, via scanning of encoded data generated by the target object).

In some embodiments, the target object is a mobile computing or communications device (e.g., smartphone, tablet) capable of establishing a wireless link to the smart device (e.g., via an application running on the mobile device, which may be activated when the mobile device is within range of the smart device). The unique token may be based on data exchanged between the mobile device and the smart device.

In some embodiments, the exchanged data includes timestamp data corresponding to the sterilization cycle. For example, timestamp data from the mobile device may correspond to, and thus verify, timestamp data from the smart device. The unique token may incorporate both sets of time data and memorialize the exchange of data.

In some embodiments, the exchanged data includes location data corresponding to the sterilization cycle. For example, location data from the mobile device may correspond to, and thus verify, location data from the smart device. The unique token may incorporate both sets of location data and memorialize the exchange of data.

In some embodiments, the unique token incorporates portions independently generated by the smart device and portions independently generated by the mobile device (the portions compiled by the smart device).

In some embodiments, the mobile computing device includes sensors (e.g., cameras, scanners) capable of identifying the smart device by detecting or scanning indicators (e.g., QR codes or other encoded data) within the sterilization chamber, and the unique token incorporates the captured images or scanned data.

In some embodiments, the smart device includes an external input device (e.g., touchscreen, keypad) capable of accepting control input from a user.

In some embodiments, when the object tray or receptacle is secured within the sterilization chamber, the smart device articulates or pivots the object receptacle to optimally expose the surfaces of the target object to disinfecting radiation.

In some embodiments, the target object may be held within the object receptacle by one or more brackets contacting the target object at several points. When the object receptacle is retracted within the sterilization chamber for the sterilization cycle, the object receptacle may be articulated such that the target object is held within the object receptacle by one or more alternative brackets, and the previously concealed points of contact on the surface of the target object may be irradiated.

In some embodiments, when the object tray or receptacle is secured within the sterilization chamber, the smart device articulates or pivots the illuminators to optimally expose the surfaces of the target object to disinfecting radiation.

In some embodiments, the interior of the sterilization chamber includes reflectors or reflective surfaces for redirecting emitted disinfecting radiation.

In some embodiments, the smart device self-diagnoses its capability to fulfill selected sterilization cycles by calibrating the emissions of the illuminators as well as the articulation of the illuminators and object receptacle.

In some embodiments, the smart device further includes a specialized testing device for calibrating illuminator and object receptacle operations. For example, the testing device is insertable into the object receptacle and includes inertial sensors to track the orientation of the testing device during a sterilization cycle. Similarly, the testing device includes radiation and luminosity sensors for checking the intensity of the disinfecting radiation emitted by the illuminators.

In a further aspect, a method for certified sterilization of a personal mobile computing or communications device is disclosed. In embodiments, the method includes placing the mobile device within a fully or partially enclosed chamber within a smart sterilization device. The method includes establishing a wireless link between the mobile device and the sterilizing device. The method includes initiating a sterilization cycle via the sterilizing device based on, e.g., the size or identity of the mobile device. The method includes irradiating the mobile device via fluorescent irradiators within the sterilization chamber according to the predetermined sterilization cycle (e.g., disinfecting radiation of a particular wavelength and luminous intensity for a particular time period). The method includes, when the sterilization cycle successfully completes, generating a unique token memorializing the completion of the sterilization cycle upon the mobile device.

In some embodiments, the method includes uniquely identifying the sterilizing device via an application configured to execute on the mobile device.

In some embodiments, the method includes optimizing, or maximizing, the surface area of the mobile device exposed to disinfecting radiation by articulating the illuminators and/or the object receptacle.

In some embodiments, the method includes generating the unique token based on timestamp data or location data exchanged between the mobile device and the sterilizing device. For example, timestamp or location data of the mobile device corresponds to timestamp or location data of the sterilizing device and verifies the presence of the mobile device for the sterilization cycle.

In some embodiments, the method includes generating the unique token based on 1) portions independently generated by the sterilizing device and 2) portions independently generated by the mobile device, the portions compiled by the sterilizing device into the unique token.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims. In the drawings:

FIG. 2A is an isometric view of a top-loading embodiment of the smart device of FIG. 1;

FIG. 2B is an isometric view of an embodiment of the smart device of FIG. 1 incorporating interior shelving or multiple-object storage;

DETAILED DESCRIPTION

Figure 1:
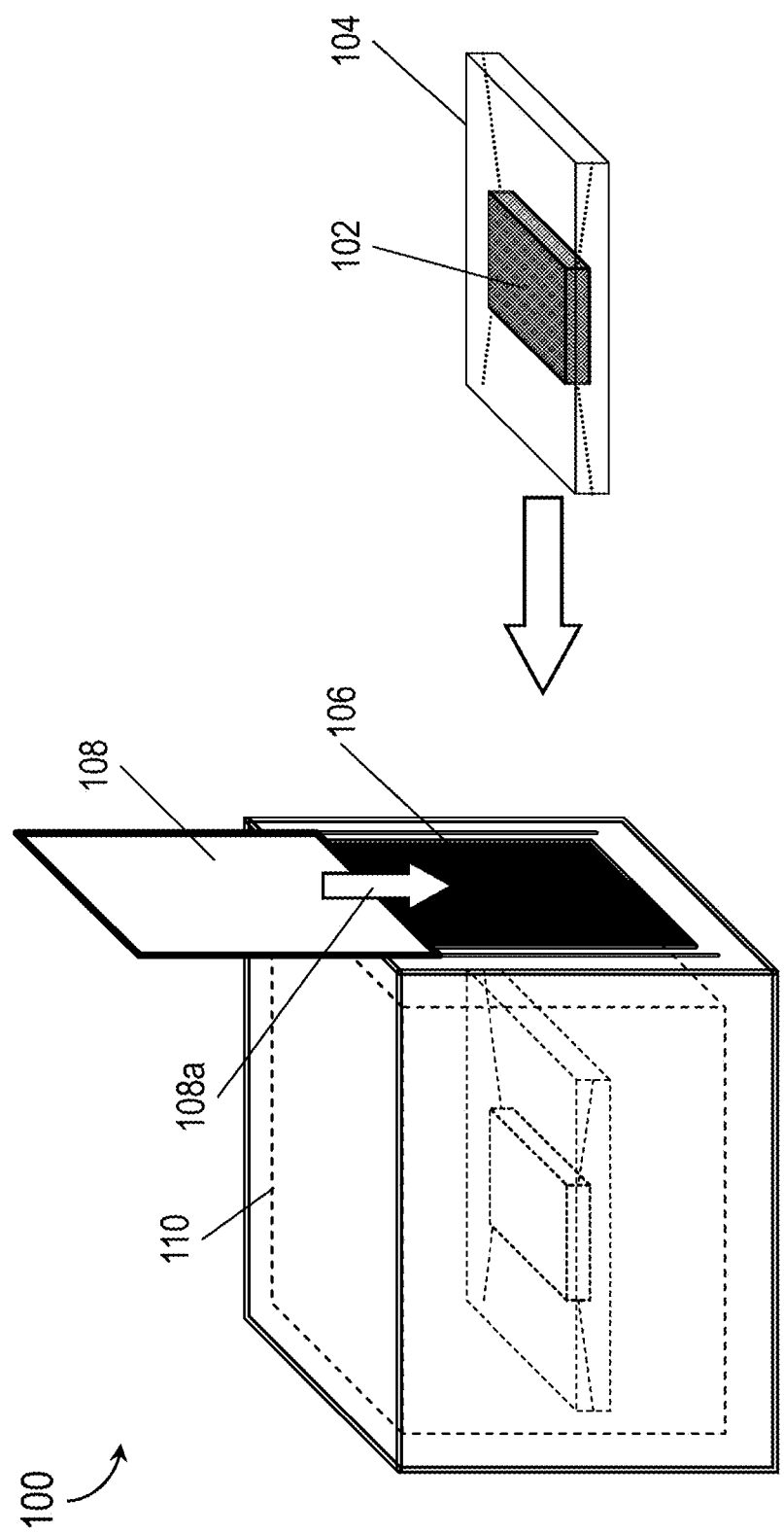
FIG. 1 is an isometric view of a smart device for certified sterilization of a mobile computing device or like personal effect according to embodiments of the inventive concepts disclosed herein.

Before explaining one or more embodiments of the disclosure in detail, it is to be understood that the embodiments are not limited in their application to the details of construction and the arrangement of the components or steps or methodologies set forth in the following description or illustrated in the drawings. In the following detailed description of embodiments, numerous specific details may be set forth in order to provide a more thorough understanding of the disclosure. However, it will be apparent to one of ordinary skill in the art having the benefit of the instant disclosure that the embodiments disclosed herein may be practiced without some of these specific details. In other instances, well-known features may not be described in detail to avoid unnecessarily complicating the instant disclosure.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only and should not be construed to limit the disclosure in any way unless expressly stated to the contrary.

Further, unless expressly stated to the contrary, "or" refers to an inclusive or and not to an exclusive or. For example, a condition A or B is satisfied by any one of the following:

A is true (or present) and B is false (or not present), A is false (or not present) and B is true (or present), and both A and B are true (or present).

In addition, use of "a" or "an" may be employed to describe elements and components of embodiments disclosed herein. This is done merely for convenience and "a" and "an" are intended to include "one" or "at least one," and the singular also includes the plural unless it is obvious that it is meant otherwise.

Finally, as used herein any reference to "one embodiment" or "some embodiments" means that a particular element, feature, structure, or characteristic described in connection with the embodiment is included in at least one embodiment disclosed herein. The appearances of the phrase "in some embodiments" in various places in the specification are not necessarily all referring to the same embodiment, and embodiments may include one or more of the features expressly described or inherently present herein, or any combination or sub-combination of two or more such features, along with any other features which may not necessarily be expressly described or inherently present in the instant disclosure.

Broadly speaking, a smart device and method for certified sterilization of personal mobile communications devices or other personal objects is disclosed. The device or object may be placed in an enclosed sterilization chamber and irradiated with ultraviolet-C (UV-C) and/or other like disinfecting radiation according to a preprogrammed sterilization cycle. When the cycle is complete, the apparatus verifies for the device (or, e.g., its owner or user) that the sterilization cycle has completed, providing the owner or user with unique documentation ensuring that the device or object has been sufficiently sterilized.

The apparatus may include control processors, onboard memory, and/or location sensors such that when a proximate mobile device has been identified (to the extent that this is possible) and the sterilization cycle completes, a record will be generated certifying that the complete sterilization cycle was performed upon the said mobile device at a particular time and/or location. In some embodiments, the apparatus may wirelessly receive accurate time and location information from an external source. The generated sterilization record may be stored onboard the apparatus or in cloud-based storage with which the apparatus is in communication, and/or forwarded to the mobile device itself for retention by its owner as an official record to certify that the mobile device was duly sterilized at the indicated time and place. In some embodiments, sterilization records, device identifiers, and the like may be encrypted or otherwise protected in compliance with data security and/or data privacy regulations as applicable.

Referring to FIG. 1, a smart device 100 for certified sterilization of a target object 102 is shown. The smart device 100 may include an object receptacle 104, slot 106, access door 108, and sterilization chamber 110.

In embodiments, the smart device 100 may be a tabletop or desktop-sized device configured to accept a personal computing device, e.g., a smartphone, tablet, phablet or like computing device, or a similarly sized personal object as the target object 102. For example, the target object 102 may be placed on or in the object receptacle 104 and retracted into a sterilization chamber 110 within the housing of the smart device 100. Once secured inside the sterilization chamber 110, the smart device 100 may initiate a sterilization cycle according to preprogrammed parameters and irradiate the target object 102 with UV-C or other disinfecting radiation. In embodiments, once a sterilization cycle has successfully completed, the smart device 100 may generate a unique token verifying the completion of a particular sterilization cycle upon a particular target object. For example, the unique token may be stored to memory aboard the smart device 100 and/or shared with the owner or user of the target object 102. In some embodiments, if the target object 102 is a mobile computing device, the unique token may be transmitted to the target object for storage therein. For example, the owner or user of the mobile computing device may subsequently produce, display, or forward the unique token, e.g., to provide assurance that the device was properly sterilized by a particular smart device 100 at a particular date and time. In some embodiments, the unique token may be generated based on data exchanged between the smart device 100 and the mobile computing device.

In embodiments, the object receptacle 104 may be a tray or other vessel configured to securely hold the target object 102 in place within the sterilization chamber 110. For example, the object receptacle 104 may include brackets 104a or other attachments configured for fixing the target object 102 into place relative to the object receptacle. In some embodiments, the object receptacle 104 may allow the target object 102 to move freely relative to the object receptacle while containing the target object within the object receptacle. In some embodiments, as described in greater detail below, the object receptacle 104 and/or its components may shift position and/or orientation relative to the sterilization chamber 110 in order to optimize the total surface area of the target object 102 exposed to disinfecting radiation by exposing outer surfaces of the target object that may have been obscured by the object receptacle, e.g., when the target object was first placed into the object receptacle or when the object receptacle was first retracted into the sterilization chamber. In some embodiments, the object receptacle 104 may be partially or fully fashioned of transparent materials configured to allow disinfecting radiation to pass through to the target object 102. In some embodiments, the object receptacle 104 may be configured to accommodate straps, handles, and/or other attachments, e.g., if the target object 102 is a mobile computing device within a protective case (the case, rather than the housing of the device, being the surface to be disinfected). In some embodiments, the smart device 100 may be capable of accepting and sterilizing other target objects 102 and non-electronic personal items of a given size (e.g., eyeglasses, jewelry, timepieces, utensils, and like effects).

In embodiments, the object receptacle 104 may be manually retracted into the sterilization chamber 110; in other embodiments, the object receptacle may be automatically retracted into the sterilization chamber, e.g., via electronically and/or mechanically assisted means. For example, the object receptacle 104 may be motorized such that a user of the smart device 100 may press a button or otherwise cause the object receptacle to retract into the sterilization chamber 110.

In some embodiments, the access door 108 may close or be closed upon retraction of the object receptacle 104 into the sterilization chamber 110 via the slot 106. For example, the access door 108 may close or be closed (108a) to enclose or seal the sterilization chamber 110, or to prevent any disinfecting radiation from escaping the sterilization chamber through the slot 106 where a user may be exposed thereto. In some embodiments, the access door 108 may be hinged, or the access door may slide along tracks or runners, opening to provide access to the sterilization chamber 110 and closing to partially or fully seal the sterilization chamber. In embodiments, the successful closure of the access door 108 may be detected by the smart device 100, after which the smart device 100 may proceed with the initialization of a sterilization cycle.

In some embodiments, the smart device 100 may be scaled up or down, e.g., sized for mobile computing or communications devices with swappable tray or receptacle components to accommodate a variety of makes or models. For example, the smart device 100 may be a portable apparatus capable of transport and use within a motor vehicle, powered by plugging into an electrical outlet of the vehicle.

Referring also to FIG. 2A, the smart device may be a top-loading or "toaster-style" apparatus. For example, the target object 102 may be inserted downward into the sterilization chamber 110. In some embodiments, upon a successful completion of the sterilization cycle, the smart device 100 may include a motorized object receptacle (104, FIG. 1) configured for articulating the sterilized target object (102a) out of the sterilization chamber 110, and beyond the outer housing of the apparatus, where the owner or user may retrieve the sterilized target object.

In some embodiments, the smart device 100 may include, instead of an object receptacle (104, FIG. 1) capable of articulating relative to the housing of the smart device, an interior slot 202 into which the target object 102 can be manually inserted for certified sterilization, and from which the target object 102 can be manually removed upon completion of a sterilization cycle. For example, the interior slot 202 may include a wireframe tray which may be fashioned from thin material (or, e.g., UV-transparent or translucent material) and which may support the target object (102b) within the sterilization chamber 110 during execution of the sterilization cycle.

In some embodiments, referring in particular to FIG. 2B, the smart device 100 may include (e.g., within the sterilization chamber 110) multiple shelves 204 (e.g., trays, slots) wherein each shelf may be capable of accommodating multiple mobile devices 102c-e, which may collectively be placed within the smart device for certified sterilization. For example, if multiple mobile devices 102c-e collectively undergo a completed sterilization cycle within the smart device 100, the smart device may log the completed sterilization cycle, identify each participating mobile device 102c-e, and generate individual records of the sterilization cycle for each participating mobile device. In embodiments, while records of a certified sterilization cycle generated and logged by the smart device of a collective sterilization cycle may uniquely identify each participating mobile device 102c-e, individual records of the completed sterilization cycle for each participating mobile device 102c-e (e.g., which may be generated at least in part jointly with the mobile device in question) may or may not identify other participating mobile devices 102d, 102e to the mobile device 102c or its user.

Referring generally to FIGS. 3A through 3D, the smart device 100 is shown.

Figure 3A:
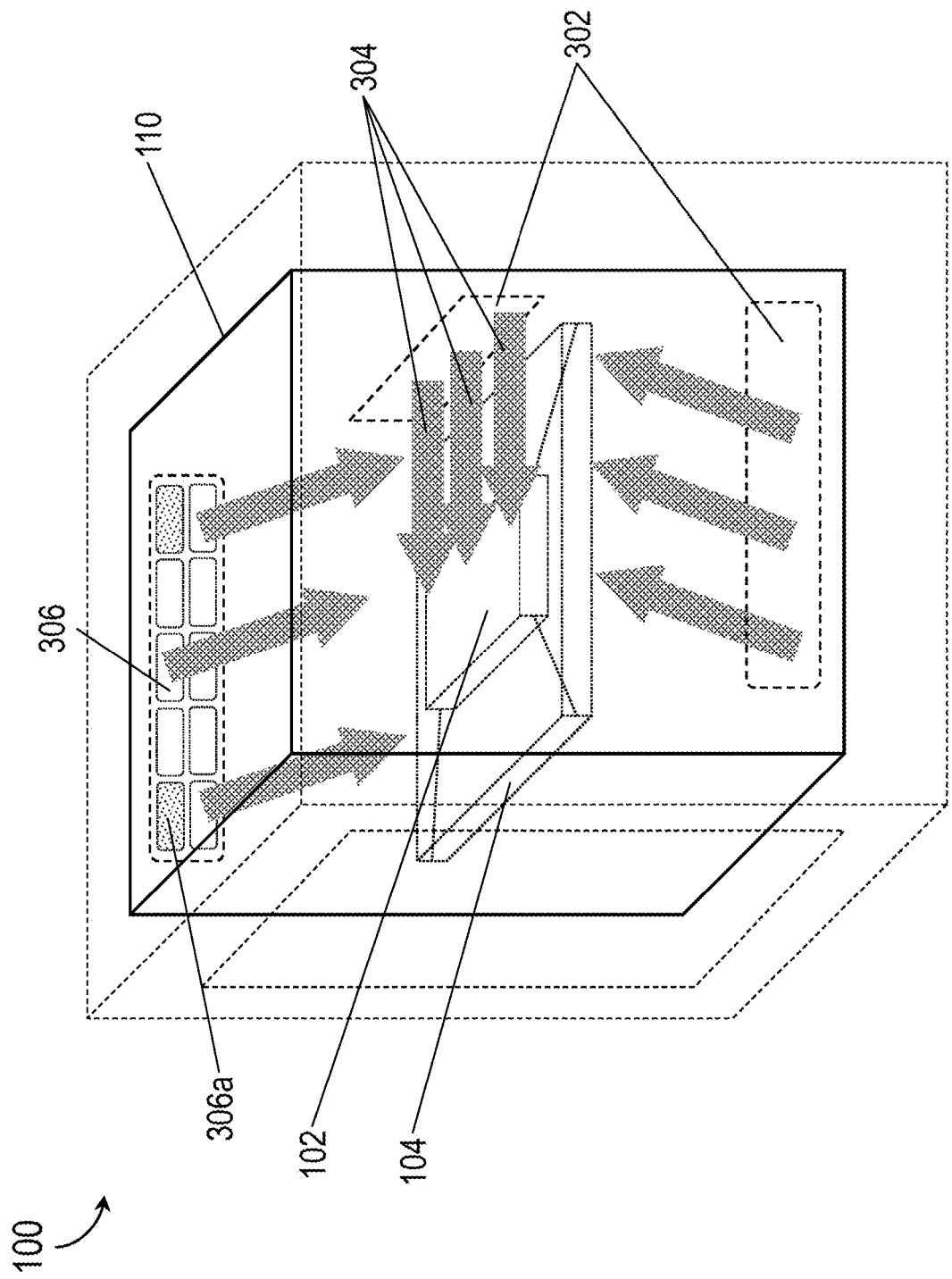
FIGS. 3A through 3D are isometric views of the smart device of FIG. 1 and operations thereof.

In embodiments, referring in particular to FIG. 3A, the smart device 100 may include illuminators 302 (e.g., irradiators) positioned within the sterilization chamber 110. For example, each illuminator 302 may be configured to emit UV-C or other like disinfecting radiation 304 at one or more desirable wavelengths and/or a predetermined light intensity level. For example, the ability to disinfect the target object 102 may be a function of radiant fluence, or the radiant energy received by a surface of the target object per unit of area (e.g., joules per square meter ($J/m^2$)). For a given target object, the likelihood that a desired percentage of pathogens (e.g., 90%) may be inactivated by irradiation may depend on a target light intensity over a particular period of time (e.g., X $J/m^2$ for Y minutes). Further, while UV-C radiation between 200 nm and 280 nm may be generally effective against pathogens, the application of different particular wavelengths may be ideally effective against different pathogens (e.g., H1N1/influenza, SARS-CoV-2 or other coronaviruses, hepatitis, tuberculosis).

In embodiments, upon initiation of a sterilization cycle (e.g., sterilization program) by the smart device 100, the illuminators 302 may be configured to emit disinfecting radiation 304 as provided by the sterilization cycle. For example, a user may select a particular sterilization cycle based on a target pathogen the user wishes to guard against, e.g., SARS-CoV-2. The selected sterilization cycle or program may provide for irradiation of the target object 102 using light of a predetermined wavelength at a predetermined intensity for a predetermined time period.

In embodiments, one or more of the illuminators 302 may comprise individual illuminator units 306, each illuminator unit 306 configured for emission of disinfecting radiation 304 at one or more particular frequencies or frequency ranges. For example, if the selected sterilization cycle is configured to inactivate H1N1 influenza virus via the application of disinfecting radiation 304 at a wavelength of 222 nm. When the sterilization cycle is initiated, the illuminator units 306 configured to emit at 222 nm may be activated while illuminator units not configured for 222 nm may remain dormant (306a). In some embodiments, either the illuminators 302 and/or illuminator units 306 may comprise multiple individual emitters, such that the activation of the illuminator or illuminator unit may result in the emission of disinfecting radiation 304 at more than one desired wavelength.

It is contemplated that human contact with the interior components of the smart device 100 and/or the sterilization chamber 110 may not be necessary during normal operations (excepting, e.g., service operations or component replacement). For example, the object receptacle 104, illuminators 302, and/or individual illuminator units 306 may be modular and/or quick-connecting in nature, such that illuminator and/or receptacle components may be quickly removed and replaced (e.g., unplugged from/plugged into a power and/or data port). In some embodiments, the sterilization chamber 110 may not be fully sealed; for example, the target object 102 may be inserted into the object receptacle 104, which may retract "toaster-style" into the smart device 100 (or may be manually retracted by the user) for initiation of the irradiation cycle and may return the sterilized target object to the user or owner when the sterilization cycle is completed and memorialized. In some embodiments, the object receptacle 104 may remain in a fixed position and orientation within the sterilization chamber 110.

Figure 3B:
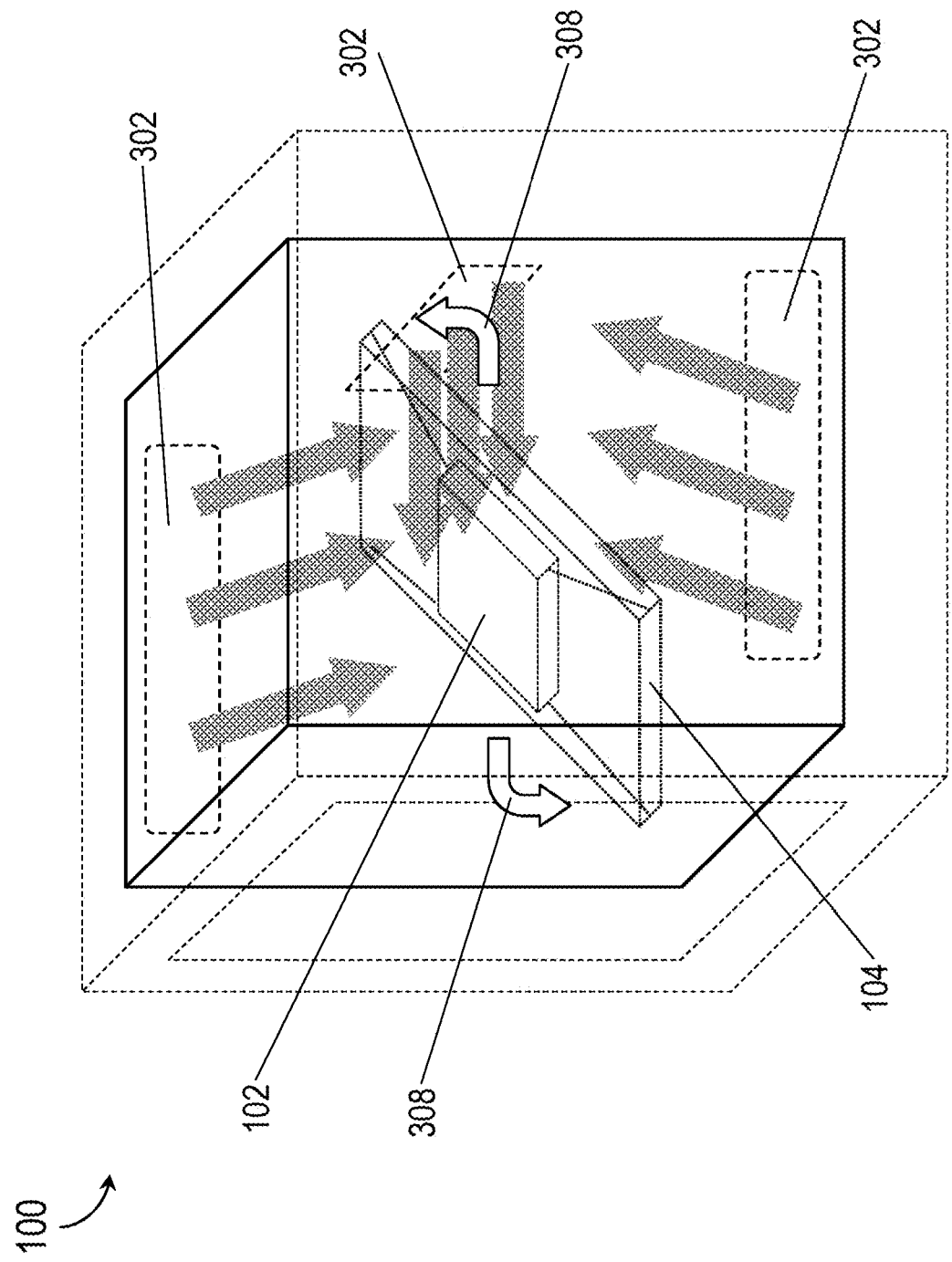

Referring now to FIG. 3B, in embodiments the object receptacle 104 may be configured for articulation (308) to optimize the irradiated surface area of the target object 102. For example, the target object 102 of FIG. 3A may experience uneven irradiation across its surface area due to the placement of the illuminators 302. Accordingly, the smart device 100 of FIG. 3B may provide for, during the course of a sterilization cycle, predetermined movement (308) of the object receptacle 104 in order to expose new surfaces of the target object 102 contained within to the illuminators 302 for a sufficient time period.

Figure 3C:
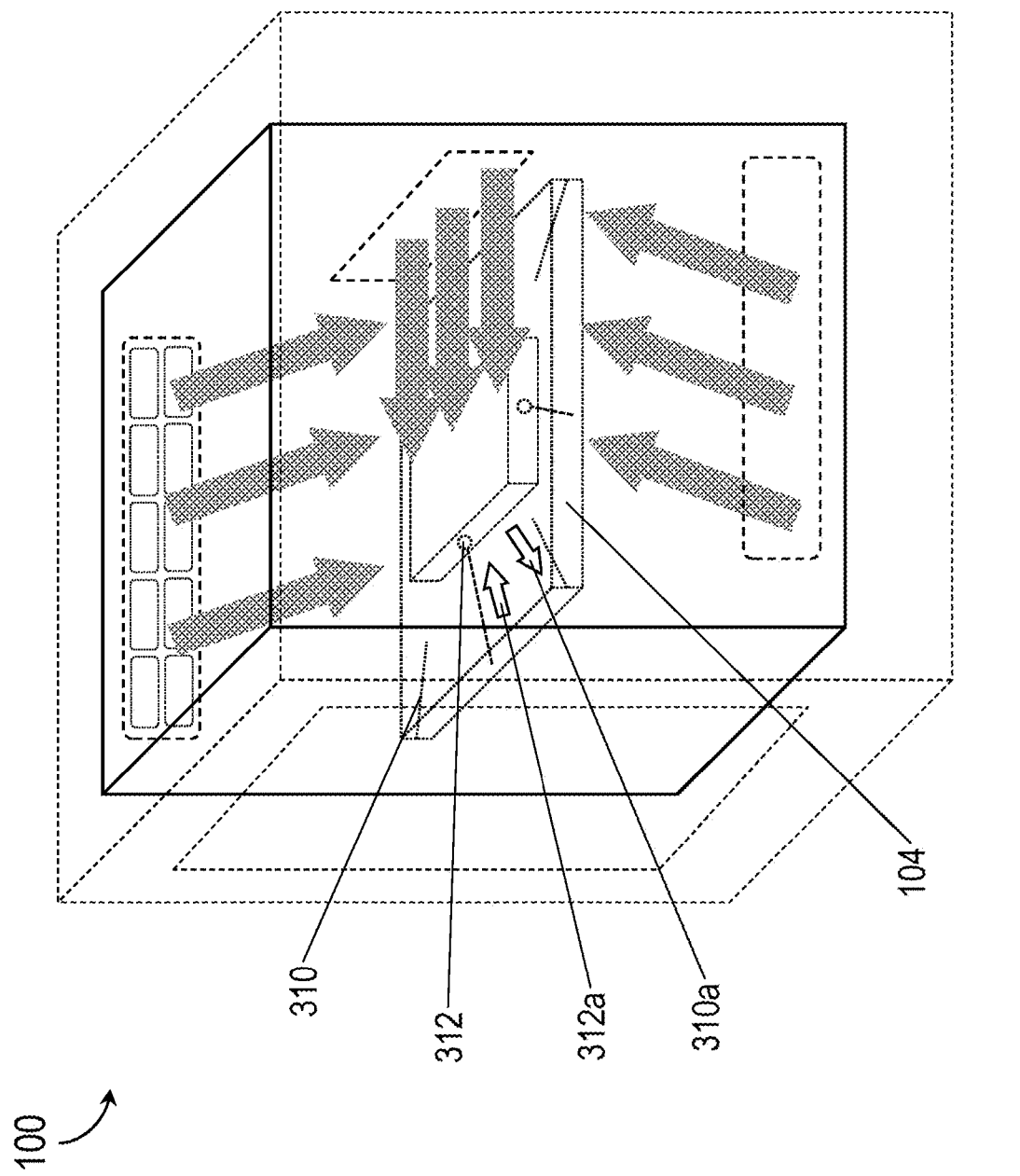

Referring now to FIG. 3C, the object receptacle 104 may comprise brackets 310 or holders configured to secure the target object 102 in place within the object receptacle, e.g., by attaching to the exterior surface or housing of the target object. In some embodiments, the smart device 100 may provide, while executing a sterilization cycle, that the brackets 310 may retract or detach (310a) from the target object 102 and that auxiliary brackets 312 attach (312a) to the target object, to ensure that any portions of the surface area of the target object that would otherwise be obscured by the brackets 310 are sufficiently irradiated.

Figure 3D:
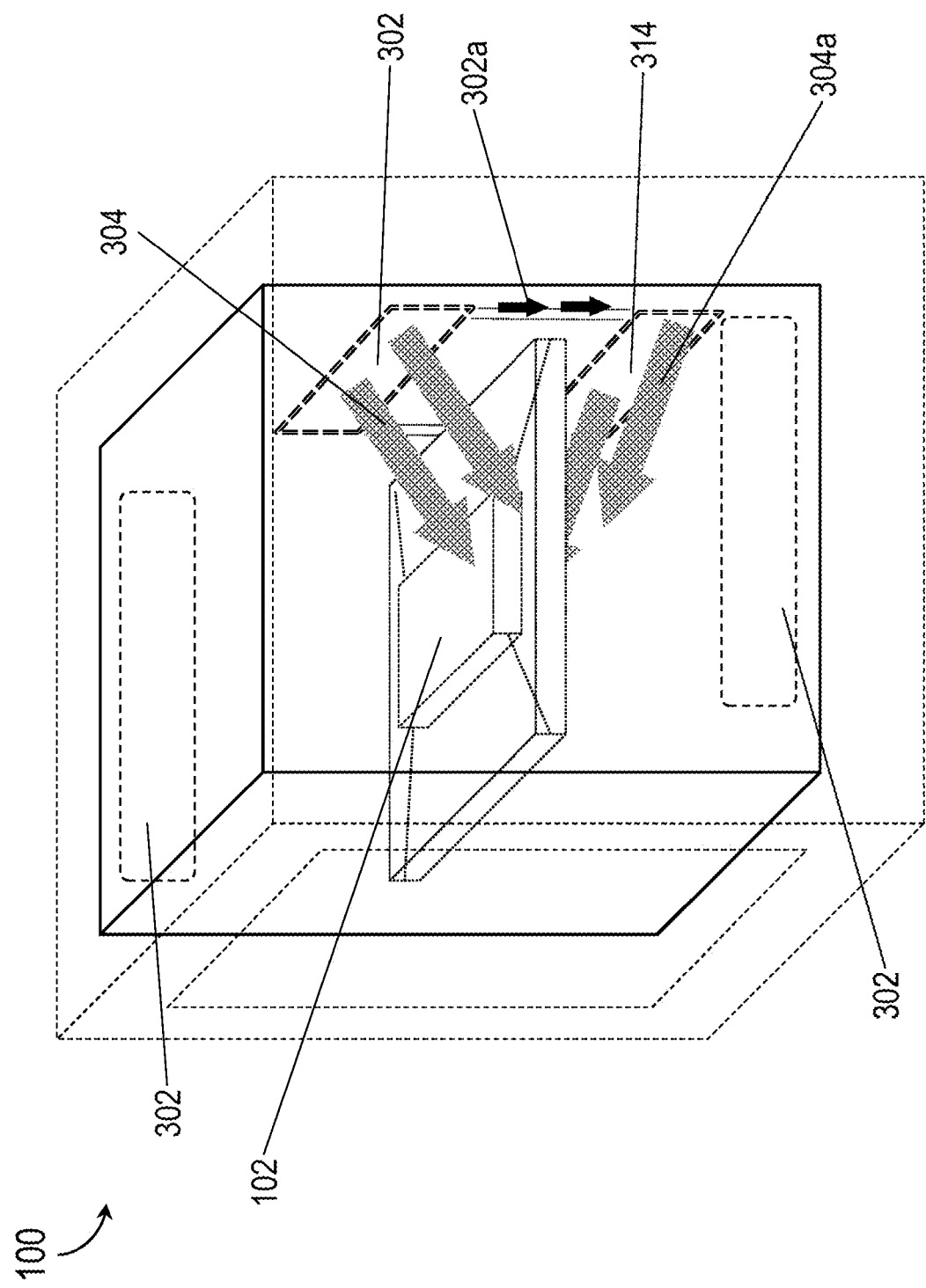

Referring now to FIG. 3D, in some embodiments the smart device 100 may optimize the irradiated surface area of the target object 102 by, during a sterilization cycle and provided for by the associated sterilization program, articulating (302a) one or more illuminators 302 from an initial position and orientation (e.g., associated with an initial coverage area for emitted disinfecting radiation 304 relative to the target object) to a subsequent position and orientation 314, via which the illuminator may direct disinfecting radiation (304a) toward new or previously nonirradiated portions of the target object 102.

Figure 4:
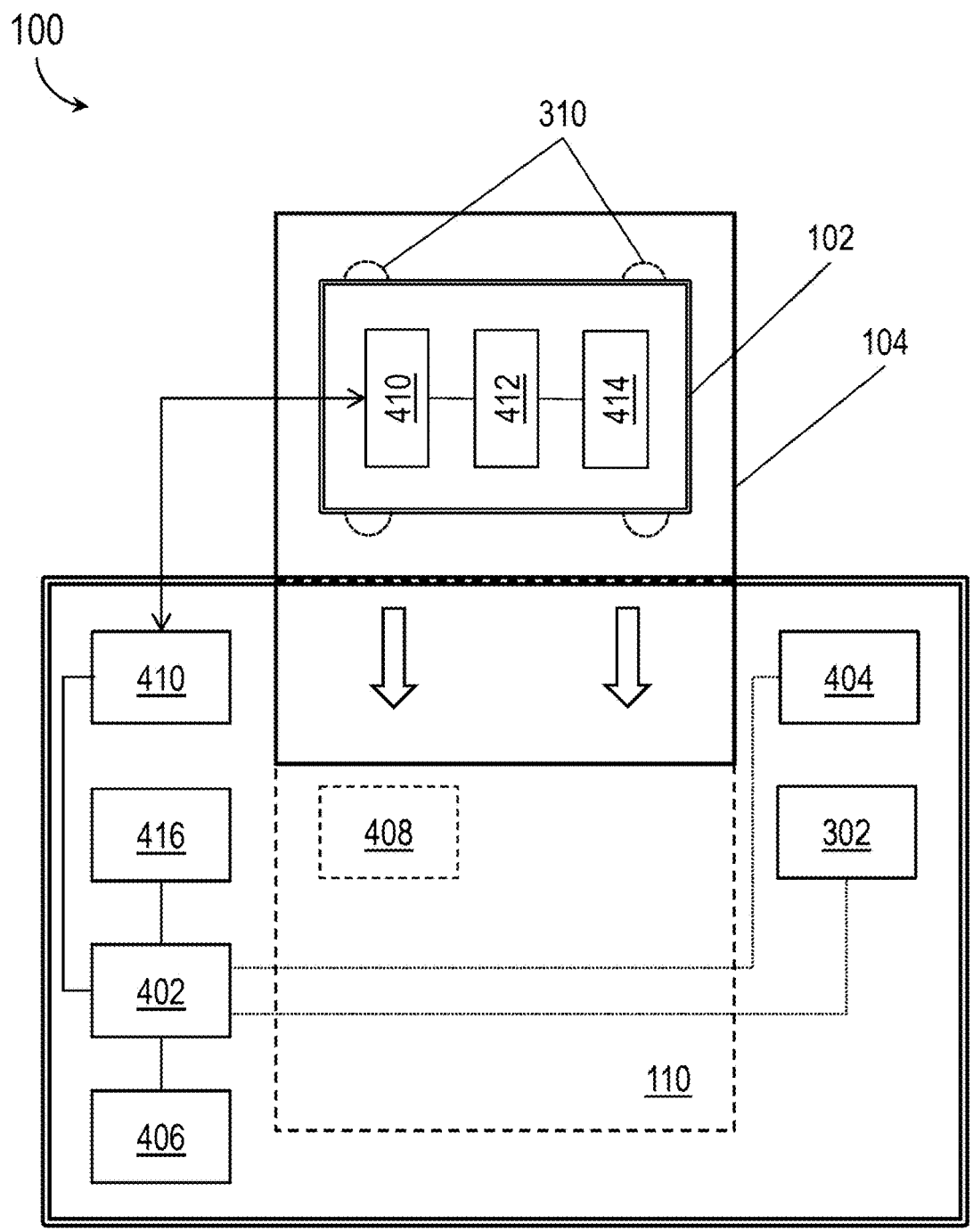
FIG. 4 is a block diagram illustrating the smart device of FIG. 1 and its components.

Referring now to FIG. 4, the smart device 100 is shown. In embodiments, the apparatus may include (in addition to the object receptacle 104, sterilization chamber 110, illuminators 302, and brackets 310), control processors 402, internal/external sensors 404, input device 406, and indicators 408.

In embodiments, the smart device 100 may initiate and execute a sterilization cycle, sterilizing the target object introduced into the sterilization chamber 110 via the object receptacle 104. For example, a user or owner of the target object 102 may select a particular sterilization cycle based on a desired target pathogen to inactivate (e.g., particular pathogens may be associated with particular wavelengths best observed to inactivate said pathogens). The manual input device 406 (e.g., a keypad, touchscreen, voice recognition system, or like system for receiving and decoding control input from the user) may present the user with several sterilization cycles from which to select. In some embodiments, the manual input device 406 may include a display system for presenting visual, auditory, and/or haptic indicators associated with a sterilization cycle, e.g., an indication that the sterilization cycle has commenced, a progress indication, an indication that the sterilization cycle has successfully completed.

In embodiments, the control processors 402 may direct the activation and/or articulation of the object receptacle 104 and/or illuminators 302 according to the predetermined or preprogrammed sterilization cycle currently under execution. For example, a selected sterilization cycle may provide that the illuminators 302 emit disinfecting radiation (304, FIG. 3A) at or including radiation of wavelength 222 nm for 8 minutes, rotating the object receptacle 180 degrees relative to its y-axis after 4 minutes to ensure that the exterior surfaces of the target object 102 are optimally exposed to radiation of sufficient fluence, e.g., to inactivate 90 percent of the selected pathogen/s.

In embodiments, the control processors 402 may verify that the selected sterilization cycle has completed and generate a unique token memorializing the execution of the selected sterilization cycle upon the target object 102. For example, the sensors 404 may include interior or exterior cameras configured for photographing the target object 102 before, during, and/or after the sterilization cycle. Images captured by the sensors 404 may be incorporated into the unique token to positively and uniquely identify the target object 102 to the extent possible.

In embodiments, the target object 102 may be a mobile computing or communications device, e.g., tablet, smartphone, phablet, mobile terminal device. For example, the smart device 100 and the target object 102 may establish a wireless link (410) via which the apparatus and target object 102 may uniquely identify each other and exchange data pursuant to the sterilization cycle.

In embodiments, the smart device 100 and target object 102 may identify each other via wireless protocol (e.g., Bluetooth, near field communication), such that a link 410 is established when the apparatus and target object are sufficiently proximate to each other. For example, an application 412 configured to execute on the processors of the target object 102 may activate (e.g., manually, if activated by the user, or automatically, when the target object is proximate to, and detects, the smart device 100 via its onboard sensors 414). The application 412 may allow the user to select a sterilization cycle for execution (e.g., based on prior sterilizations of the target object 102), and may uniquely identify the smart device 100 based on exchanged information (e.g., a wallet ID or other unique identifier).

In embodiments, the smart device 100 and target object 102 may jointly generate the unique token memorializing the completion of the selected sterilization cycle. For example, based on identifying data exchanged via the link 410, the control processors 402 and the processors of the target object 102 may each independently generate ledger-based transaction records documenting the sterilization cycle. The control processors 402 may compile its own transaction records, as well as those generated by the target object 102 and shared via the link 410, into the unique token. The resulting unique token may be stored to onboard memory 416 and transmitted to the target object 102 via the application 412. In some embodiments, the unique token may be a blockchain-type record forwarded to a central ledger remotely located from the smart device 100 (e.g., the central ledger associated with a network of smart device 100) and protected from retroactive alteration.

In embodiments, either or both of the smart device 100 and the mobile device 102 may memorialize each completed sterilization cycle by as many associated data points are available to that device (or, e.g., the two devices may jointly do so as described below). For example, a record of a completed sterilization cycle may uniquely identify (e.g., or attempt to identify) the smart device 100 or mobile device 102, the sterilization status (e.g., a particular cycle selected, requested, or recommended; whether said cycle was successfully completed; if not completed, any available error messages indicating why), as well as date, time, and/or location information associated with the sterilization cycle as recorded or sensed by either or both devices.

In embodiments, either or both of the smart device 100 and the mobile device 102 may log records of sterilization cycles with which they are associated, either via storage in onboard memory of either device or by uploading sterilization cycle records to blockchain-based, cloud-based, network-based, or other remote storage. For example, the smart device 100 may be a publicly available device in which a user of a mobile device 102 may not want to store private records associated with sterilization cycles involving the mobile device.

In some embodiments, sterilization cycle records may include information about the user of the mobile device 102. For example, a network of smart devices 100 may collectively store their sterilization records (e.g., in a central data storage location or via cloud/blockchain/distributed data storage remote from any individual smart device) and may track individual mobile devices 102 and/or their users throughout the network (e.g., for contact tracing purposes).

User information may include, but is not limited to, login credentials, biometric identifiers, and/or employee ID tags or devices (e.g., including swipable strips or chips, scannable encoded data, and/or RFID identifier tags unique to the employee).

In some embodiments, the smart device 100 (e.g., or a network of said smart devices) may be trained (e.g., via guided analysis of training data or machine learning techniques) to analyze device and user information and adjust the performance of the smart device accordingly. For example, the smart device 100 may conclude that a particular user and/or mobile device 102 consistently selects a particular sterilization cycle; should the user encounter another smart device within the network, the "favorite" sterilization cycle may be suggested even if the user or mobile device has had no previous contact with the particular smart device.

In embodiments the smart device 100 (and/or a network of said devices) may be provided with, and may analyze user data, to recommend a new sterilization cycle or program to a particular mobile device 102 or user. For example, the user may be known to community-based contract tracing programs to have been in contact with, or proximate to, individuals identified by said program as sick, infected, or otherwise contaminated, the user may be known (e.g., based on user location data) to have frequented health care facilities or to have recently traveled to an at-risk area, or the user may be identified as working in an at-risk field generally.

Similarly, in some embodiments the smart device 100 may access public health data (e.g., at national, state, community levels) to track likely pathogens or contaminants present within the community at a given time. Accordingly, the smart device 100 may prescribe to the user sterilization cycles or programs more suitable to the likely level of, and potential origins of, contamination risk associated with the user, e.g., in terms of radiation intensity, exposure time, or radiation type (e.g., increased irradiation times or specific component wavelengths of the disinfecting radiation based on likely contaminants).

In some embodiments, the object receptacle 104 may be configured for inductive charging of a target object 102 (e.g., a mobile computing device configured for inductive charging). For example, the smart device 100 may be set to an "overnight mode" whereby a target object 102 placed within the sterilization chamber 110 may be recharged and sterilized over an extended period of time (e.g., several hours, as opposed to a sterilization cycle generally having a duration of several minutes). In some embodiments, the smart device 100 may include (e.g., within the sterilization chamber 110 or object receptacle 104) ports, docking, and/or cabling for physical charging of any mobile devices 102 placed therein for sterilization. In some embodiments, these ports, docking, or cabling may be externally attached.

In embodiments, the sensors 404, 414 may include clocks and location sensors configured to determine precise time and location information relevant to a sterilization cycle. For example, the sensors 404 of the smart device 100 may include clocks and positioning systems, such that the unique token includes accurate time information of the sterilization cycle (e.g., a time of initiation, a time of duration, a time of completion, a time of synchronization with the target object 102) and an accurate location of the smart device 100 corresponding to the sterilization cycle (e.g., to the initiation and/or successful completion).

In some embodiments, the sensors 414 of the target object 102 may similarly include clocks and positioning systems (e.g., clocks and positioning systems of a mobile computing device). For example, the unique token memorializing the sterilization cycle may include time and location data from the target object 102 as well as from the smart device 100. It may be observed that the smart device 100 may be portable but may in practice be installed at a fixed location, such that location data corresponding to the apparatus may remain relatively consistent over time and may therefore serve as a control. In embodiments, the target object 102 (e.g., via the application 412) may similarly capture precise time and location information via its own sensors 414, such that the unique token may verify the presence of the target object 102 at a consistent location (e.g., consistent with the location of the smart device 100) at a time corresponding to the sterilization cycle (e.g., as documented by the time sensors 404 of the smart device 100).

Figure 5A:
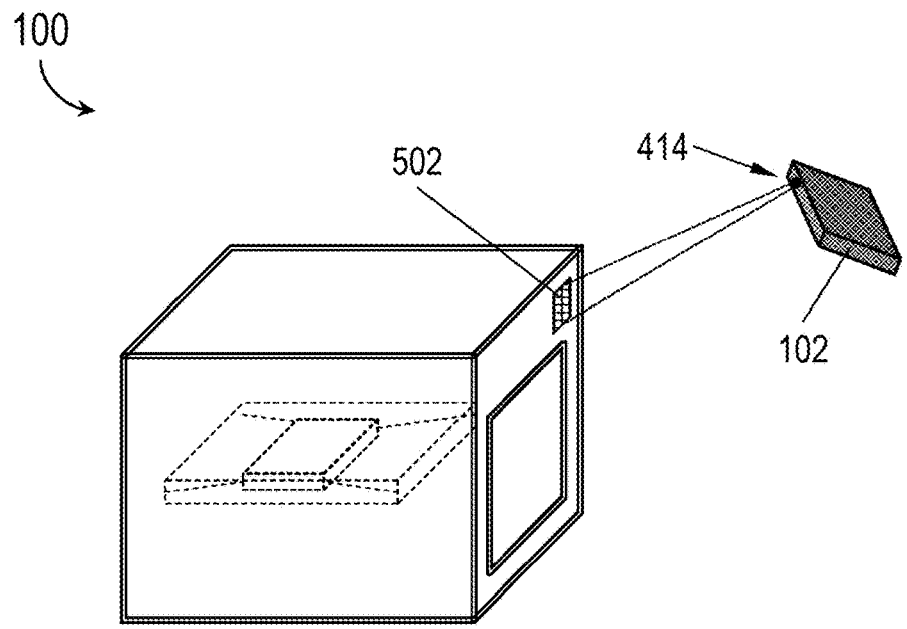
FIGS. 5A through 5D are isometric views illustrating the smart device of FIG. 1 and operations thereof.
Figure 5B:
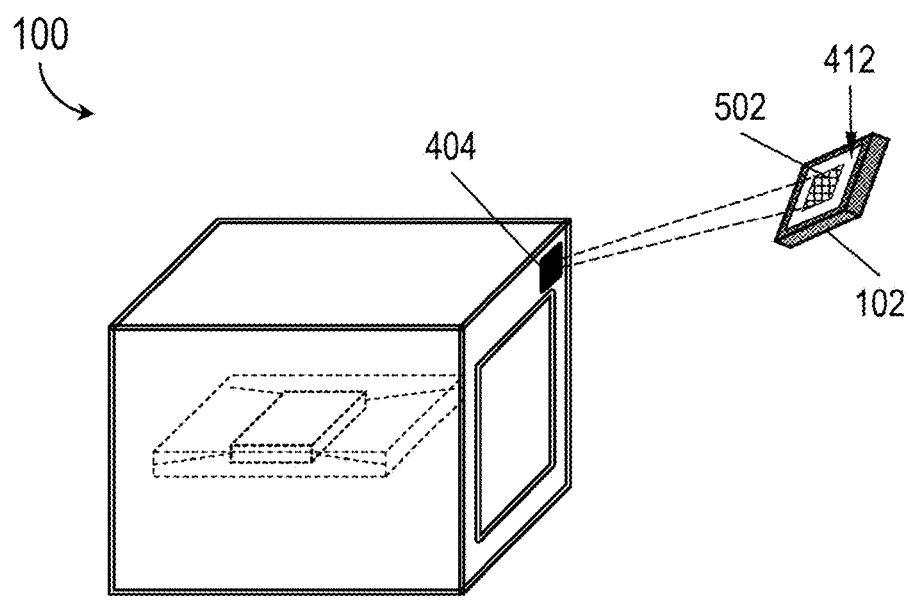
Figure 5C:
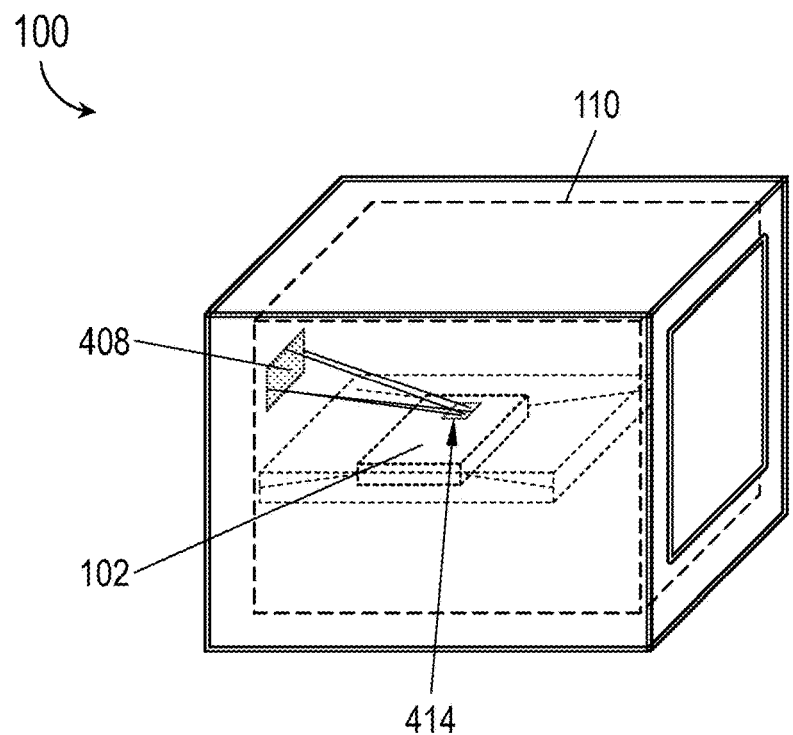

In embodiments, referring to FIGS. 5A through 5C, the sensors 404, 414 may include cameras or scanners configured for detecting the smart device 100 or target object 102 via encoded information. For example, referring in particular to FIG. 5A, the smart device 100 may include QR codes, bar codes, RFID tags, or other encoded data 502 attached to an exterior surface, such that the sensors 414 of the target object 102 may uniquely identify the smart device 100 or otherwise initiate an interaction with the apparatus by decoding the encoded data. In some embodiments, referring in particular to FIG. 4B, the application 412 executing on the target object 102 may generate encoded data 502 scannable by the external sensors 404 of the smart device 100. In some embodiments, the target object 102 may attempt to pair with the smart device 100, e.g., upon detection or scanning of encoded data 502, or upon entering a range proximate to the smart device 100. For example, any target objects 102 having previously paired with the smart device 100 (e.g., for prior sterilization cycles) may attempt to pair with the smart device 100 upon being returned to its proximity. In some embodiments, one or both of the smart device 100 and the target object 102 may display a unique code or icon (e.g., alphanumeric, graphic) confirming, or prompting for confirmation, that the target object and smart device are paired, e.g., for wireless exchange of operational information.

In some embodiments, referring in particular to FIG. 5C, the indicators 408 may be attached to an interior surface of the sterilization chamber 110 and may include similarly encoded data unique to the smart device 100. For example, the target object 102 (e.g., as directed by the application 412) may photograph or scan the indicators 408 (via sensors 414) during the course of the sterilization cycle to document the sterilization cycle.

Figure 5D:
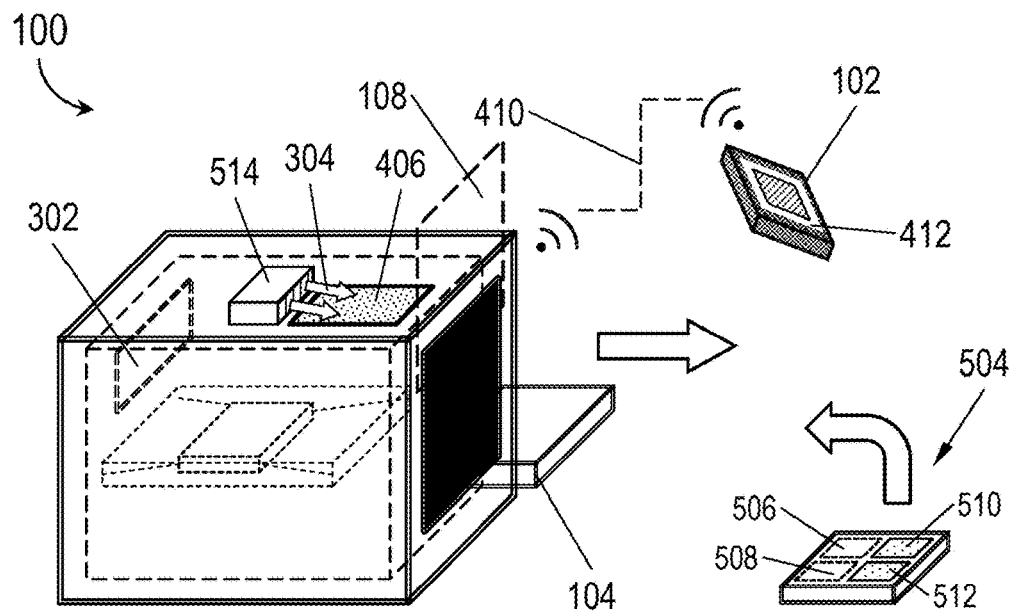

In some embodiments, referring to FIG. 5D, establishing a link 410 between the smart device 100 and the target object 102 may trigger one or more operations in the apparatus and/or target object. For example, the application 412 may launch on the target object 102, prompting the user to acknowledge the identification of the smart device 100 and select a sterilization cycle for execution (e.g., if the target object has been sterilized by the apparatus before, the user may be prompted based on a stored history of interaction between the target object and apparatus). Similarly, upon establishing the link 410, the smart device 100 may call up its stored history of interaction with the target object 102, such that the user may select a sterilization cycle based on past interactions via the input device 406. In addition, the access door 108 may open and the object receptacle 104 may extend from within the smart device 100, such that the user may place the target object 102 within the object receptacle.

In some embodiments, the smart device 100 may execute self-calibration or self-diagnostic procedures when no sterilization operations are ongoing or expected (e.g., during off-hours). For example, the smart device 100 may provide that self-calibration and/or self-diagnostic procedures as disclosed below must be regularly performed (e.g., at predetermined intervals, such as every two months) to ensure that the apparatus is able to effectively sterilize objects according to its predetermined sterilization cycles (e.g., that the apparatus is able to generate disinfecting radiation (304, FIG. 3A) of the required fluence for the required time period).

In embodiments, the control processors (402, FIG. 4) may test the object receptacle 104 as well as each illuminator 302 and/or individual illuminator unit (306, FIG. 3A) to ensure proper tray operations and expected irradiation of any target objects 102 placed in the object receptacle. In some embodiments, a specialized testing device 504 may be placed within the object receptacle to facilitate calibration or diagnostic operations. For example, the specialized testing device 504 may include a wireless transceiver 506 for establishing a wireless link (410, FIG. 4) with the smart device 100, e.g., for testing data connectivity and exchange. The specialized testing device 504 may include accelerometers or other inertial sensors 508, e.g., for tracking movement of the object receptacle 104 during a diagnostic cycle as opposed to expected movement. The specialized testing device 504 may include luminosity sensors 510 for verifying luminous intensity of the illuminators 302 and/or individual illuminator units 306. The specialized testing device may include a visual/image sensor 512, e.g., a camera or scanner for verifying the accessibility of any scannable indicators (408, FIG. 5C) within the sterilization chamber 110, or for recording the full diagnostic cycle from within the sterilization chamber for later review.

In some embodiments, the smart device 100 may include an external illuminator 514. For example, the external illuminator 514 may activate to disinfect the input device 406 or any other high contact surfaces of the smart device 100 via emission of disinfecting radiation 304 according to a predetermined sterilization cycle. In embodiments, the external illuminator 514 may be configured for operation only when the smart device 100 is unattended, e.g., off-hours or overnight when users are not anticipated.

Figure 6:
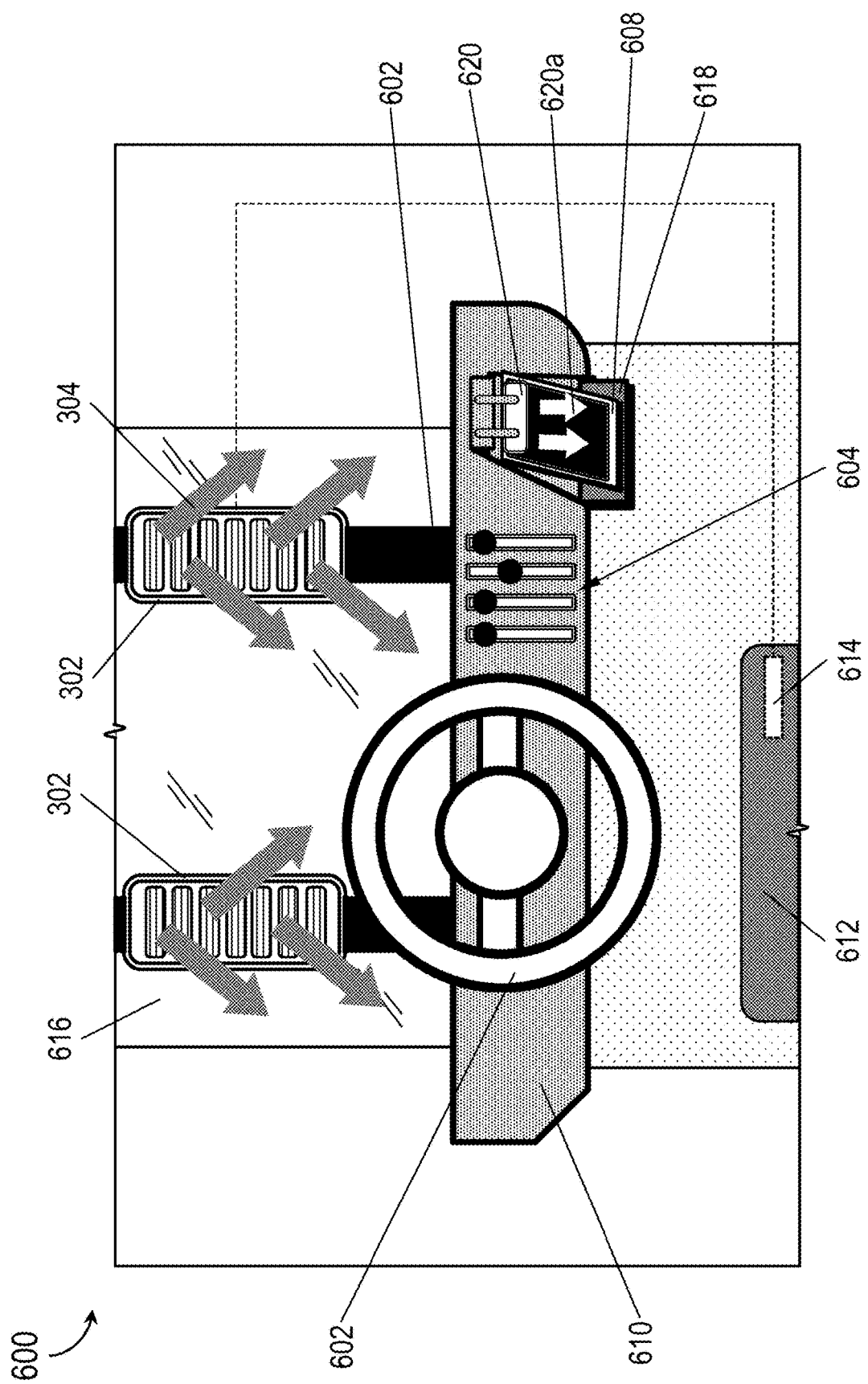
FIG. 6 is an overhead view of a forklift implementation of the smart device of FIG. 1.

Referring now to FIG. 6, the smart device 600 may be implemented and may function similarly to the smart device 100 of FIGS. 1 through 5D, except that the smart device 600 may be configured for sterilization of an interior portion of a forklift or other like vehicle.

In embodiments, the smart device 600 may include illuminators 302 mounted to an exterior strut 602 or structure and oriented toward the operator cabin. For example, the operator cabin may include a steering wheel 604, manual controls 606, input terminals or mobile devices 608, dashboard 610, and operator seat 612, all of which may come into contact with multiple operators throughout the day and thus may be a potential vehicle for transmission of pathogens.

In embodiments, the operator seat 612 may include sensors 614 to determine, e.g., via sensed weight or strain of at least a threshold amount, whether or not an operator is currently seated in the operator seat. For example, when the sensors 614 indicate that the operator seat 612 has not been occupied for a predetermined amount of time, a sterilization cycle may be initiated.

In embodiments, when a sterilization cycle is initiated by the smart device 600, the illuminators 302 may emit disinfecting radiation 304 for a predetermined amount of time sufficient to inactivate a threshold amount (e.g., 90%, 95%) of pathogens by irradiating, e.g., the dashboard 610, steering wheel 604, manual controls 606, input terminals/mobile devices 608, and operator seat 612. In some embodiments, the smart device 600 may include a shroud or similar cover deployable by a user exiting the operator cabin, e.g., to at least partially cover the operator cabin and/or windshield 616 and prevent disinfecting radiation 304 from escaping the operator cabin. In some embodiments, the smart device 600 may include an alert configured to generate visual and/or auditory warnings when a sterilization cycle is initiated or imminent, e.g., to warn any individuals in the vicinity of the forklift not to approach or enter the operator cabin while the sterilization cycle is in progress.

In some embodiments, the dashboard 610 may include a dock 618 configured for securing the mobile device 608 (and, e.g., providing a physical link for the mobile device into a local network or subsystem of the forklift or vehicle). For example, the dock 618 may position and/or orient the mobile device 608 in such a way that the mobile device may be easily viewed by an operator of the forklift from the operator seat 612. However, in this position and orientation the mobile device 608 (in particular, a touchscreen 608a thereof) may be oriented away from the illuminators 302, or partially/fully obscured from the illuminators by the dock 618. In embodiments, the smart device 600 may include additional or auxiliary illuminators 620 oriented to irradiate (620a) the mobile device 608 as positioned in the dock 618.

Figure 7:
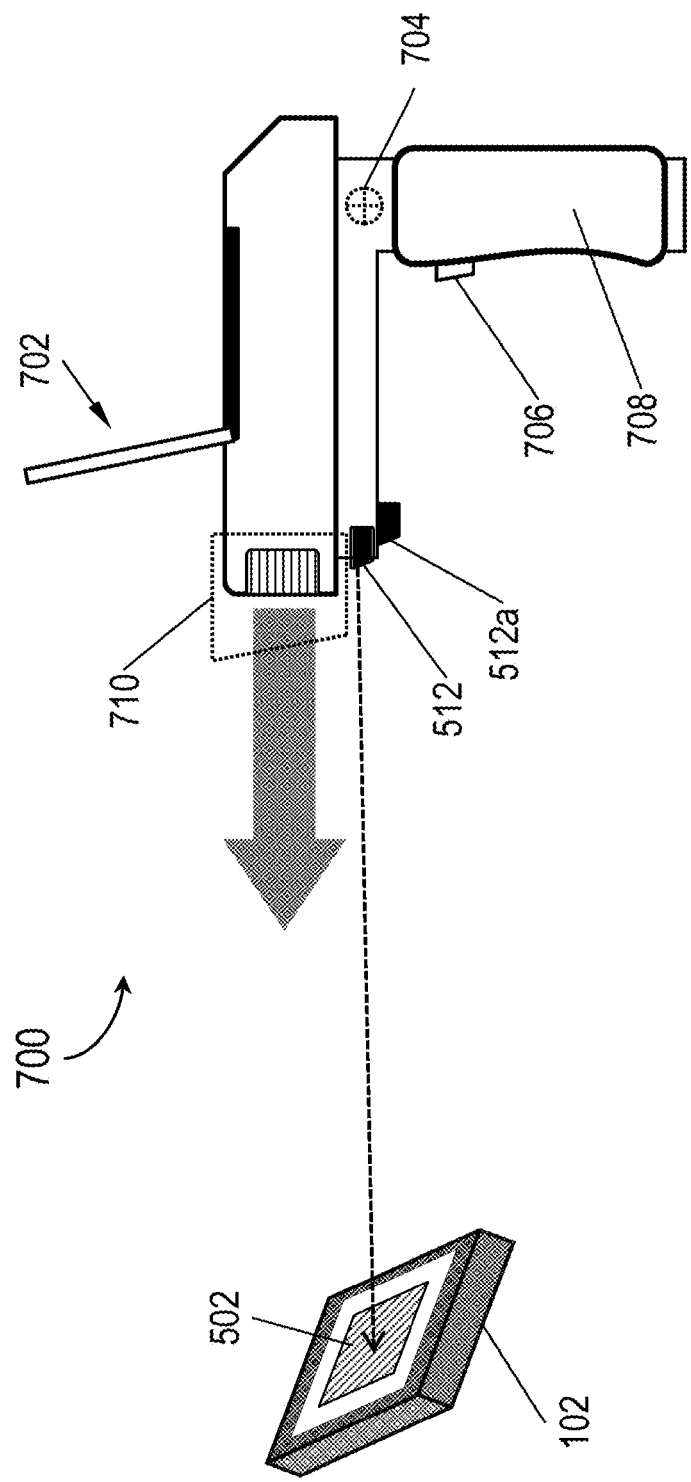
FIG. 7 is an illustration of a handheld implementation of the smart device of FIG. 1.

Referring now to FIG. 7, the smart device 700 may be implemented and may function similarly to the smart device 100 of FIGS. 1 through 5D, except that the smart device 700 may be a handheld device.

In embodiments, the smart device 700 may be aimed at the target object 102. For example, the smart device 700 may include one or more visual sensors (scanner 512, camera 512a) for identifying the target object 102 (e.g., via QR code or like encoded data 502 generated by an application (412, FIG. 4), if the target object is a mobile computing device). In embodiments, the apparatus 700 may include a display screen 702. For example, the display screen 702 may present to the user a menu of sterilization cycles from which to select, and may aid or prompt the user through the execution of a selected sterilization cycle (e.g., by displaying a time remaining for predetermined irradiation of the target object 102, or alerting the user if inertial sensors 704 determine that the orientation of the smart device 700 has diverged from its aim on the target object 102). In some embodiments, the camera 512a may activate to document the full sterilization cycle in real time.

In embodiments, a sterilization cycle may be initiated manually (e.g., via the display screen 702, if the display screen is touch-sensitive, or via a trigger 706 or button set into the handle 708 of the smart device 700) or automatically, once a link (410, FIG. 4) has been established to the target object 102.

In embodiments, the smart device 700 may include a shroud 710 surrounding the illuminator 302. For example, the shroud 710 may provide partial protection to the user from disinfecting radiation 304, directing emitted radiation toward the target object 102. In some embodiments, the display screen 702 may flip upward from the surface of the smart device 700 and provide the user additional protection.

Figure 8:
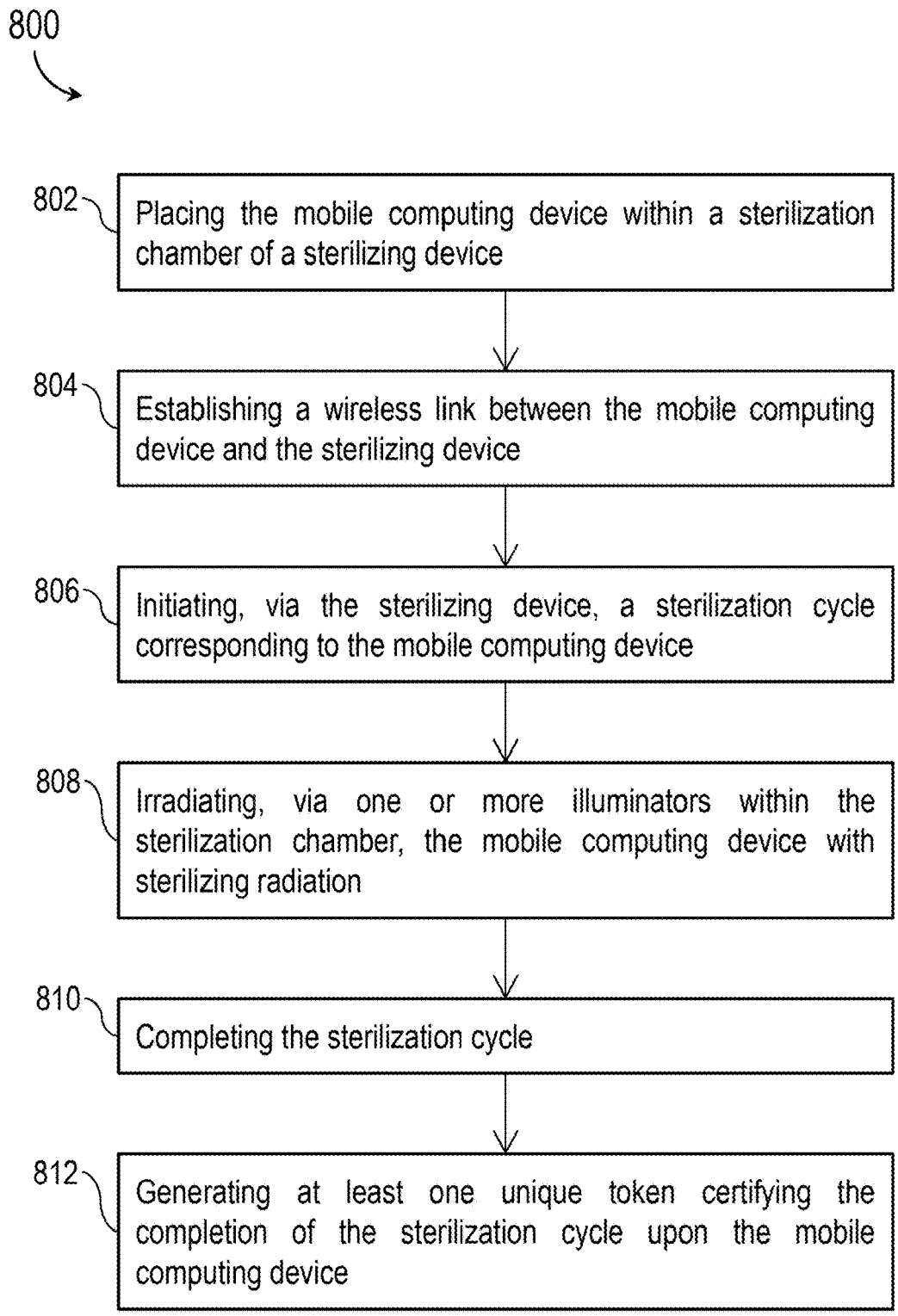
FIG. 8 is a process flow diagram illustrating a method for certified sterilization of a mobile computing device according to embodiments of the inventive concepts disclosed herein.

Referring to FIG. 8, the method 800 may be implemented by the smart device 100, and may include the following steps.

At a step 802, a mobile computing device (e.g., smartphone, tablet, phablet) is placed within a sterilization chamber, the sterilization chamber partially or fully enclosed within the smart device.

At a step 804, the smart device establishes a wireless link to the mobile computing device. In some embodiments, the link may activate (or the user may manually activate) an application configured to execute on the mobile computing device; the application establishes a data link to the smart device and uniquely identifies the mobile computing device to the smart device.

At a step 806, the smart device initiates a sterilization cycle based on the mobile computing device. In some embodiments, a specific sterilization cycle is chosen by the user (via the smart device or via an application executing on the mobile device).

At a step 808, illuminators within the sterilization chamber irradiate the mobile computing device with disinfecting radiation at one or more desired wavelengths for a predetermined time period. In some embodiments, either or both of the illuminators or the object receptacle securing the mobile computing device within the sterilization chamber articulate or pivot to maximize the surface area of the mobile computing device exposed to disinfecting radiation.

At a step 810, the smart device completes the sterilization cycle. For example, the sterilization cycle may complete upon the expiration of the predetermined elapsed time for irradiation.

At a step 812, the smart device generates a unique token memorializing the completion of the sterilization cycle upon the uniquely identified mobile computing device. In some embodiments, the mobile computing device and the smart device exchange location and timestamp data to verify the location of the mobile device within the smart device at the time of the sterilization cycle. In some embodiments, some portions of the unique token are generated by the smart device and other portions by the mobile computing device, the portions compiled into the unique token by the smart device.

CONCLUSION

It is to be understood that embodiments of the methods disclosed herein may include one or more of the steps described herein. Further, such steps may be carried out in any desired order and two or more of the steps may be carried out simultaneously with one another. Two or more of the steps disclosed herein may be combined in a single step, and in some embodiments, one or more of the steps may be carried out as two or more sub-steps. Further, other steps or sub-steps may be carried in addition to, or as substitutes to one or more of the steps disclosed herein.

Although inventive concepts have been described with reference to the embodiments illustrated in the attached drawing figures, equivalents may be employed and substitutions made herein without departing from the scope of the claims. Components illustrated and described herein are merely examples of a system/device and components that may be used to implement embodiments of the inventive concepts and may be replaced with other devices and components without departing from the scope of the claims. Furthermore, any dimensions, degrees, and/or numerical ranges provided herein are to be understood as non-limiting examples unless otherwise specified in the claims.

I claim:

1. An apparatus for certified sterilization of personal items, comprising:
a housing enclosing a sterilization chamber;
an object receptacle at least partially within the sterilization chamber and configured to accept a target object to be sterilized;
one or more external sensors mounted to the housing, the one or more external sensors configured to detect and uniquely identify the target object;
one or more illuminators disposed within the sterilization chamber, the one or more illuminators configured to direct disinfecting radiation at the target object according to a sterilization cycle;
and
one or more processors operatively coupled to the one or more illuminators, the one or more processors configured to:
initiate the sterilization cycle by activating the one or more illuminators;
and
upon completion of the sterilization cycle, generate at least one unique token certifying the completion and corresponding to the identified target object.

2. The apparatus of claim 1, wherein the target object includes a mobile computing device comprising one or more mobile processors, wherein the one or more processors are configured to:
establish a wireless link to the target object via an application configured to execute on the mobile processors;
and
generate the at least one unique token based on information exchanged between the apparatus and the target object.

3. The apparatus of claim 2, wherein:
the one or more processors are configured to generate first time data corresponding to the completed sterilization cycle;
and
the information exchanged between the apparatus and the target object comprises:
the first time data;
second time data generated by the target object and corresponding to the completed sterilization cycle;
and
at least one verification of an exchange of one or more of the first time data or the second time data.

4. The apparatus of claim 2, wherein:
the one or more processors are configured to generate first location data corresponding to a location of the apparatus during the sterilization cycle;
and
the information exchanged between the apparatus and the target object comprises:
the first location data;
second location data generated by the target object and corresponding to a location of the target object during the sterilization cycle;
and
at least one verification of an exchange of one or more of the first location data or the second location data.

5. The apparatus of claim 2, wherein the at least one unique token comprises:
at least one first portion generated by the one or more processors;
and
at least one second portion generated by the one or more mobile processors.

6. The apparatus of claim 2, wherein:
the mobile computing device comprises one or more sensors;
the apparatus further comprises at least one indicator attached to an interior surface of the sterilization chamber and detectable by the one or more sensors;
and
the at least one unique token includes at least one verification of the indicator via the one or more sensors.

7. The apparatus of claim 1, further comprising:
at least one input device operatively coupled to the one or more processors and configured for accepting control input from the user, the control input including data corresponding to the target object.

8. The apparatus of claim 1, wherein:
the object receptacle is articulable between at least:
a first configuration, wherein the object receptacle extends outside the housing, and wherein a user may insert or remove the target object into or from the object receptacle;
and
a second configuration, wherein the object receptacle is enclosed by the sterilization chamber;
and
wherein the one or more processors are configured to:
when the object receptacle is in the second configuration, adjust at least one of a position of the object receptacle or an orientation of the object receptacle by articulating the object receptacle according to the sterilization cycle.

9. The apparatus of claim 8, wherein:
the first configuration of the object receptacle is associated with one or more first points of contact with the target object;
and
the one or more processors are configured to irradiate the one or more first points of contact according to the sterilization cycle by articulating the object receptacle such that the second configuration is associated with one or more second points of contact with the target object.

10. The apparatus of claim 8, wherein the one or more processors are configured to calibrate one or more of:
irradiation operations of the one or more illuminators;
articulating the one or more illuminators;
or
articulating the object receptacle.

11. The apparatus of claim 10, further comprising:
a testing device insertable in the object receptacle, the testing device comprising:
at least one inertial sensor configured to sense an orientation of the testing device;
at least one radiation sensor configured to detect the disinfecting radiation emitted by the one or more illuminators.

12. The apparatus of claim 1, wherein the one or more processors are configured to irradiate the target object according to the sterilization cycle by articulating the one or more illuminators.

13. The apparatus of claim 1, further comprising:
one or more reflectors attached to an interior surface of the sterilization chamber, the one or more reflectors configured to redirect the emitted disinfecting radiation.

14. A method for certified sterilization of a mobile computing device, the method comprising:
placing the mobile computing device within a sterilization chamber of a sterilizing device;
uniquely identifying the mobile computing device via an external sensor of the sterilizing device;
establishing a wireless link between the mobile computing device and the sterilizing device;
initiating, via the sterilizing device, a sterilization cycle corresponding to the mobile computing device;
irradiating, via one or more illuminators within the sterilization chamber, the mobile computing device with disinfecting radiation according to the sterilization cycle;
completing the sterilization cycle;
and
generating, via at least one of the sterilizing device or the mobile computing device at least one unique token certifying the completion of the sterilization cycle and corresponding to the mobile computing device.

15. The method of claim 14, wherein irradiating, via one or more illuminators within the sterilization chamber, the mobile computing device with disinfecting radiation includes:
irradiating an optimal surface area of the mobile computing device via articulating one or more of:
the one or more illuminators;
and
an object receptacle securing the mobile computing device within the sterilization chamber.

16. The method of claim 14, wherein generating at least one unique token certifying the completion of the sterilization cycle upon the mobile computing device includes:
generating the at least one unique token based on one or more of:
timestamp data exchanged by the mobile computing device and the sterilizing device;
or
location data exchanged by the mobile computing device and the sterilizing device.

17. The method of claim 14, wherein generating at least one unique token certifying the completion of the sterilization cycle upon the mobile computing device includes:
generating, via the sterilizing device, at least one first portion of the unique token;
generating, via the mobile computing device, at least one second portion of the unique token;
transmitting, via the mobile computing device, the at least one second portion to the sterilizing device;
and
compiling, via the sterilizing device, the at least one first portion and the at least one second portion.

* * * * *